United States Patent
Huang et al.

(10) Patent No.: US 8,721,919 B2
(45) Date of Patent: May 13, 2014

(54) ORGANIC-INORGANIC METAL OXIDE HYBRID RESIN, A METHOD FOR FORMING THE SAME, AND TRANSPARENT RESIN COMPOSITION FORMED THEREFROM

(71) Applicant: Industrial Technology Research Institute, Hsinchu (TW)

(72) Inventors: Shu-Chen Huang, Keelung (TW); Wen-Bin Chen, Tainan (TW); Hsun-Tien Li, Hsinchu (TW); Chia-Wen Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/670,204

(22) Filed: Nov. 6, 2012

(65) Prior Publication Data
US 2013/0334458 A1    Dec. 19, 2013

(30) Foreign Application Priority Data

Jun. 13, 2012   (TW) ............................. 101121059 A (51) Int. Cl.
*C08G 77/44* (2006.01)
*C07F 7/08* (2006.01)
*C07F 7/28* (2006.01)

(52) U.S. Cl.
CPC ..................................... *C08G 77/44* (2013.01)
USPC ........................................ 252/182.3; 556/10

(58) Field of Classification Search
CPC .................................................... C08G 77/398
USPC ........................................ 252/182.3; 556/10
See application file for complete search history.

(56) References Cited

U.S. PATENT DOCUMENTS 4,122,109 A * 10/1978  Halm ............................ 556/456

4,157,978 A * 6/1979 Llenado ....................... 510/452
(Continued)

FOREIGN PATENT DOCUMENTS

| CN | 101517009 A | 8/2009 |
|---|---|---|
| TW | 271002 | 11/1991 |

(Continued)

OTHER PUBLICATIONS

Lin, et al., "Development of High-Performance Optical Silicone for the Packaging of High-Power LEDs", IEEE Transactions on Components and Packaging Technologies, vol. 33, No. 4, Dec. 2010, pp. 761-766.

(Continued)

*Primary Examiner* — Mike M Dollinger
(74) *Attorney, Agent, or Firm* — Muncy, Geissler, Olds & Lowe, P.C.

(57) ABSTRACT

In one embodiment, an organic-inorganic metal oxide hybrid resin having the following formula:

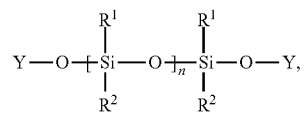

wherein each $R^1$ is independently a substituted or non-substituted $C_1$ to $C_{10}$ alkyl group; each $R^2$ is independently a substituted or non-substituted $C_1$ to $C_{10}$ alkyl group or benzyl group; n is a positive integer from 3 to 30; and each Y is independently $(MO_{4/2})_l[(MO)_{(4-a)/2}M(OH)_{a/2}]_m[MO_{(4-b)/2}M(OZ)_{b/2}]_p$, wherein M is a metal; l is a positive integer from 10 to 90; m is a positive integer from 2 to 20; p is a positive integer from 4 to 15; a is a positive integer from 1 to 2; b is a positive integer from 1 to 2; and Z is an organosilane group.

25 Claims, 2 Drawing Sheets

(56) References Cited

U.S. PATENT DOCUMENTS

| | | | |
|---|---|---|---|
| 4,322,518 A * | 3/1982 | Blizzard | 528/15 |
| 4,591,622 A * | 5/1986 | Blizzard et al. | 525/477 |
| 4,639,489 A * | 1/1987 | Aizawa et al. | 524/588 |
| 5,063,254 A * | 11/1991 | Nakos | 522/43 |
| 5,319,121 A | 6/1994 | Blum | |
| 5,391,638 A | 2/1995 | Katsoulis et al. | |
| 5,395,954 A * | 3/1995 | Soria et al. | 556/10 |
| 5,665,850 A * | 9/1997 | Priou | 528/31 |
| 5,777,433 A | 7/1998 | Lester et al. | |
| 5,843,525 A * | 12/1998 | Shibasaki et al. | 427/214 |
| 6,072,012 A * | 6/2000 | Juen et al. | 525/478 |
| 6,200,580 B1 * | 3/2001 | Horino et al. | 424/401 |
| 7,052,718 B2 * | 5/2006 | Nakade et al. | 424/489 |
| 8,440,848 B2 * | 5/2013 | Murakami et al. | 556/10 |
| 2002/0022713 A1 | 2/2002 | Tanaka et al. | |
| 2002/0172697 A1* | 11/2002 | Nakade et al. | 424/401 |
| 2003/0114630 A1 | 6/2003 | Okubo et al. | |
| 2005/0282977 A1* | 12/2005 | Stempel et al. | 525/477 |
| 2007/0116969 A1* | 5/2007 | Liu | 428/447 |
| 2007/0221939 A1 | 9/2007 | Taskar et al. | |
| 2008/0267859 A1 | 10/2008 | Abu-Omar | |
| 2009/0017280 A1 | 1/2009 | Suzuki et al. | |
| 2009/0093579 A1* | 4/2009 | Kanamori et al. | 524/430 |
| 2010/0055044 A1 | 3/2010 | Cohen | |
| 2010/0067258 A1 | 3/2010 | Hahn et al. | |
| 2010/0150513 A1 | 6/2010 | Zhang et al. | |
| 2011/0092661 A1* | 4/2011 | Lichtenhan et al. | 528/30 |

FOREIGN PATENT DOCUMENTS

| | | |
|---|---|---|
| TW | 200916503 | 4/2009 |
| TW | 201040215 | 11/2010 |

OTHER PUBLICATIONS

Su, et al., "High refractive index polyimide-nanocrystalline-titania hybrid optical materials", Journal of Materials Chemistry, 2008, 18, pp. 1139-1145

Mont, et al., "High-refractive-index Ti02-nanoparticle-loaded encapsulants for light-emitting diodes", Journal of Applied Physics, 103, 083210, 2008, 7 pages.

He, et al., "Novel epoxy-silicone thermolytic transparent packaging adhesives chemical modified by ZnO nanowires for HB LEDs", J. Nanopart Res., 2010, pp. 3019-3024

Choi, et al., "Observation of Tunable Refractive Indices and Strong Intermolecular Interactions in Newly Synthesized Methylene-biphenylene-Bridged Silsesquioxane Thin Films", J. Phys. Chem. C, 2010, 114, pp. 14233-14239.

Lee, et al., "Refractive index engineering of transparent $ZrO_2$-polydimethylsiloxane nanocomposites", Journal of Materials Chemistry, 2008, 18, pp. 1751-1755.

* cited by examiner

ORGANIC-INORGANIC METAL OXIDE HYBRID RESIN, A METHOD FOR FORMING THE SAME, AND TRANSPARENT RESIN COMPOSITION FORMED THEREFROM

CROSS REFERENCE TO RELATED APPLICATIONS

This application claims priority of Taiwan Patent Application No. 101121059, filed on Jun. 13, 2012, the entirety of which is incorporated by reference herein.

TECHNICAL FIELD

The technical field relates to an organic-inorganic metal oxide hybrid resin, a method for forming the same, and transparent resin composition formed therefrom.

BACKGROUND

The transmittance and refractive index of transparent materials are two of the main concerns when the transparent materials are used in optical displays or modules. Research related to the refractive index of materials shows that refractivity may depend on the molecular weight, density, or molar refractivity of the materials. Those materials which have a higher density, larger molar refractivity, and smaller molar volume may have a higher refractivity.

In general, to increase the refractive index of the materials, chemical synthesis or organic-inorganic dispersion techniques are required. The chemical synthesis technique includes modifying the material by performing a chemical synthesis. For example, modifying the molecule structure to include aromatic rings, halogens, sulfur, or the like can increase the refractive index of the material. However, the chemical synthesis may result in worsening the transmittance and the thermal and yellowing resistance of the material.

The organic-inorganic dispersion technique includes adding nano-inorganic oxide having a high refractive index into a transparent organic material matrix. Since the nano-inorganic oxide and the organic material matrix tend to have incompatible interfaces and the nano-inorganic oxide particles tend to assemble with each other, an intensive mechanical shearing force is usually used in a dispersion process to evenly disperse the nano-inorganic oxide particles into the organic material matrix. However, when the material contains more than 50 wt % of the nano-inorganic oxide or when the thickness of the material is larger than 100 μm, the transmittance of the material will decrease notably. Therefore, the method can only be used to prepare a thin film but can not be used to form a bulk material having a larger thickness.

Therefore, a transparent material having good transmittance and high refractive index is required.

SUMMARY

A detailed description is given in the following embodiments with reference to the accompanying drawings.

In one embodiment, an organic-inorganic metal oxide hybrid resin having the following formula:

wherein each $R^1$ is independently a substituted or non-substituted $C_1$ to $C_{10}$ alkyl group; each $R^2$ is independently a substituted or non-substituted $C_1$ to $C_{10}$ alkyl group or benzyl group; n is a positive integer from 3 to 30; and each Y is independently $(MO_{4/2})_l[(MO)_{(4-a)/2}M(OH)_{a/2}]_m[MO_{(4-b)/2}M(OZ)_{b/2}]_p$, wherein M is a metal; l is a positive integer from 10 to 90; m is a positive integer from 2 to 20; p is a positive integer from 4 to 15; a is a positive integer from 1 to 2; b is a positive integer from 1 to 2; and Z is an organosilane group.

In another embodiment, a transparent resin composite, including: 10 to 80 parts by weight of the organic-inorganic metal oxide hybrid resin described previously; and 20 to 90 parts by weight of liquid epoxy resin.

In still another embodiment, a method for forming an organic-inorganic metal oxide hybrid resin, including: performing a bonding reaction between a metallic alcoholate precursor and a polysiloxane having a terminal organic functional group, such that a compound having an oxometallate cluster structure and a structure containing repetitive siloxane units is formed; performing a sol-gel reaction by adding a catalyst and water into the compound having oxometallate cluster structures and a structure containing repetitive siloxane units to form a sol-gel product; and reacting the sol-gel product with organosilane to form an organic-inorganic metal oxide hybrid resin.

In still another embodiment, an organic-inorganic metal oxide hybrid resin formed by the following method, wherein the method includes: (1) performing a bonding reaction between a metallic alcoholate precursor and a polysiloxane having a terminal organic functional group, such that a compound having an oxometallate cluster structure and a structure containing repetitive siloxane units is formed; (2) performing a sol-gel reaction by adding a catalyst and water into the compound having oxometallate cluster structures and a structure containing repetitive siloxane units to form a sol-gel product; and (3) reacting the sol-gel product with organosilane to form an organic-inorganic metal oxide hybrid resin.

BRIEF DESCRIPTION OF THE DRAWINGS

The present disclosure can be more fully understood by reading the subsequent detailed description and examples with references made to the accompanying drawings, wherein.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

Moreover, the formation of a first feature over and on a second feature in the description that follows may include embodiments in which the first and second features are formed in direct contact, and may also include embodiments in which additional features may be formed between the first and second features, such that the first and second features may not be in direct contact.

In one embodiment, an organic-inorganic metal oxide hybrid resin and a method for forming the same are provided.

Figure 1:
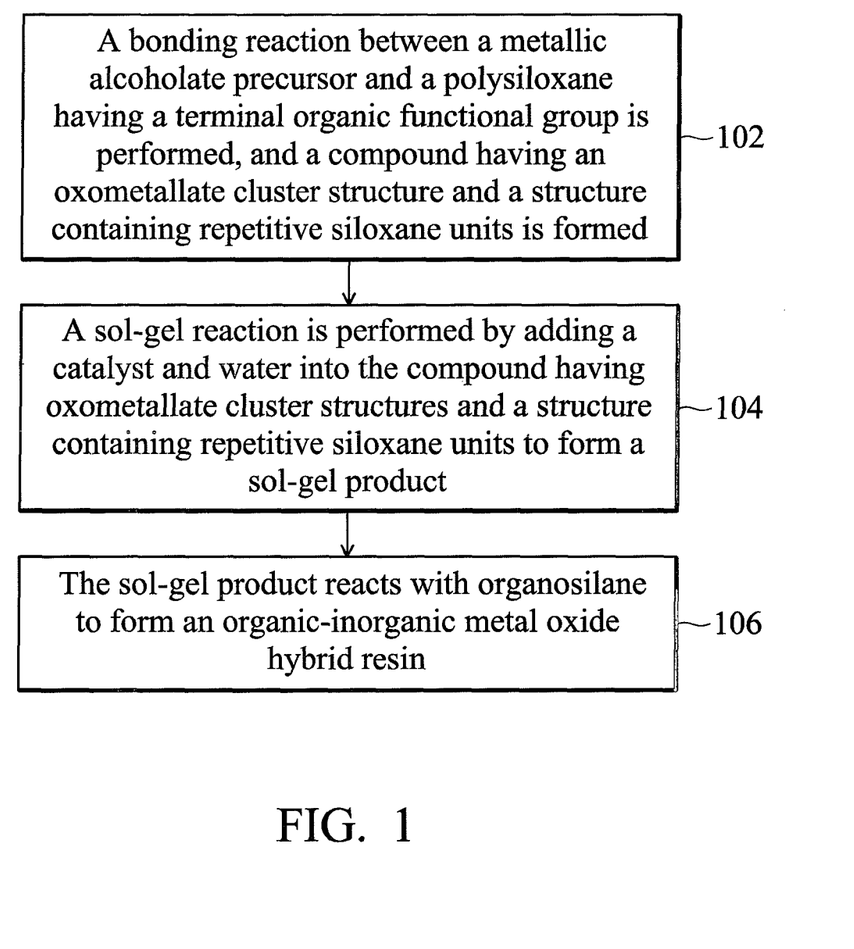
FIG. 1 illustrates a flow chart of forming an organic-inorganic metal oxide hybrid resin according to one embodiment.

FIG. 1 illustrates a flow chart of forming an organic-inorganic metal oxide hybrid resin according to one embodiment. In step 102, a bonding reaction between a metallic alcoholate precursor and a polysiloxane having a terminal organic functional group is performed, and a compound having an oxometallate cluster structure and a structure containing repetitive siloxane units is formed. In step 104, a sol-gel reaction is performed by adding a catalyst and water into the compound having oxometallate cluster structures and a structure containing repetitive siloxane units to form a sol-gel product. In step 106, the sol-gel product reacts with organosilane to form an organic-inorganic metal oxide hybrid resin.

In one embodiment, the reaction in steps 102 to 106 can be presented by the following equation (A-0). In equation (A-0), M is a metal, such as titanium (Ti), zirconium (Zr), or zinc (Zn), in a metallic alcoholate precursor. Each $R^1$ is independently a substituted or non-substituted $C_1$ to $C_{10}$ alkyl group. Each $R^2$ is independently a substituted or non-substituted $C_1$ to $C_{10}$ alkyl group or benzyl group. n is a positive integer from 3 to 30. Each $R^3$ is a $C_1$ to $C_{10}$ alkyl group containing an organic substituted group, wherein the organic substituted group comprises an expoxy group, an acrylic group, an alkenyl group, a silanol group, an amino group, or combinations thereof. In addition, $\{$ represents a bond, wherein the bond bonds to the Si or M of another organosilane group. In other words, the oxygen of the organosilane in the resulting organic-inorganic metal oxide hybrid resin may bond to the metal M or Si of another organosilane.

sol-gel products, and in the organic-inorganic metal oxide hybrid resin according to various embodiments.

Details of steps 102 to 106 are described below. Referring to step 102, a bonding reaction between a metallic alcoholate precursor and a polysiloxane having a terminal organic functional group is performed, and a compound having an oxometallate cluster structure and a structure containing repetitive siloxane units is formed. The reaction may be performed in a solvent, such as butanol, isopropyl alcohol, toluene, hexane, or combinations thereof. The reaction time may be between 48 hrs and 300 hrs. The reaction temperature may be between 25° C. and 150° C. However, these conditions are, of course, merely examples and are not intended to be limiting. In one embodiment, the polysiloxane has the following formula (A-1):

(A-1)

(A-0)

It should be noted that the equation (A-0) is merely an example. One skilled in the art would understand that the size and bonding of the oxometallate cluster structure may be varied by the compound having an oxometallate cluster structure and a structure containing repetitive siloxane units, in the In formula (A-1), $R^1$ is a substituted or non-substituted $C_1$ to $C_{10}$ alkyl group; $R^2$ is a substituted or non-substituted $C_1$ to $C_{10}$ alkyl group or benzyl group; and n is a positive integer from 3 to 30. In order to increase the refractivity of the product, the metal, which comes from the metallic alcoholate precursor, may be chosen to have its oxide be transparent under visible light and have a high refractivity. Therefore, examples of the metallic alcoholate precursor include, but are not limited to, titanium alcoholate, zirconium alcoholate, zinc alcoholate, or combinations thereof. More specifically, the metallic alcoholate precursor may, for example, be n-butyl zirconium, n-butyl titanium, n-butyl zinc, or combinations thereof.

In one embodiment, the compound having an oxometallate cluster structure and a structure containing repetitive siloxane units in step 102 may be presented by formula (A-2) (as shown below). In formula (A-2), the structure containing repetitive siloxane units (A portion) forms the main chain of the organic-inorganic metal oxide hybrid resin, and its two sides each bond to one oxometallate cluster structure (B portion) respectively. Therefore, the compound has a portion containing Si—O-M (M is a metal) bonding and other portions containing partially hydrolytic condensed oxometallate. In formula (A-2), the definition of $R^1$, $R^2$, and n are the same as in formula (A-1), and M is the metal of the metallic alcoholate precursor, such as titanium (Ti), zirconium (Zr), or zinc (Zn).

(A-2)

It should be noted that the formula (A-2) is merely an example. One skilled in the art would understand that the size and bonding of the oxometallate cluster structure may be varied by the compound having an oxometallate cluster structure and a structure containing repetitive siloxane units according to various embodiments.

Referring to step 104, a sol-gel reaction is performed by adding a catalyst and water into the compound having oxometallate cluster structures and a structure containing repetitive siloxane units to form a sol-gel product. In one embodiment, the sol-gel reaction may be performed in a solvent, such as butanol, isopropyl alcohol, toluene, hexane, or combinations thereof. In one embodiment, the reaction time of the sol-gel reaction may be between 48 hrs and 180 hrs. The reaction temperature may be between room temperature and 150° C. In another embodiment, the sol-gel reaction is first performed in a first solvent (such as butanol) at room temperature to 100° C. for 8 hrs to 120 hrs. After that, the sol-gel reaction is performed in a second solvent (such as toluene) at 110° C. to 150° C. for 60 hrs to 120 hrs. By using the sol-gel reaction includes various temperature stages, the nucleation and growth rate of the product may be controlled, and therefore the refractivity of the product may be adjusted.

Comparing the sol-gel product and the compound in step 102 (as shown in formula (A-2)), the sol-gel product also has the structure containing repetitive siloxane units as its main chain, and its two sides each bond to an oxometallate cluster structure respectively. However, the size of the oxometallate cluster structure of the sol-gel product is larger than that of formula (A-2). For example, the sol-gel product may be presented by formula (A-3) (as shown below). In formula (A-3), the definition of $R^1$, $R^2$, n, and M are the same as in formula (A-2). However, it should be noted that the formula (A-3) is merely an example. One skilled in the art would understand that the size and bonding of the oxometallate cluster structure may be various in the sol-gel products in various embodiments.

(A-3)

Referring to step 106, the sol-gel product reacts with organosilane to form an organic-inorganic metal oxide hybrid resin. The reaction time may be between 12 hrs and 24 hrs. The reaction temperature may be between 60° C. and 150° C.

However, these conditions are, of course, merely examples and are not intended to be limiting. By bonding organosilane onto the outer surface (the terminal structures) of the oxometallate cluster structures formed in step 104, the condensation of the oxometallate cluster structures may be stabilized, and their assembly may be avoided. Therefore, an organic-inorganic metal oxide hybrid resin with good stability can be formed. The organosilane may contain expoxy groups, acrylic groups, alkenyl groups, silanol groups, amino groups, or combinations thereof. In one embodiment, the organosilane may be presented by formula (A-4) (as shown below). In formula (A-4), $R^4$ is a substituted or non-substituted $C_1$ to $C_4$ straight alkyl group. $R^3$ is a $C_1$ to $C_{10}$ alkyl group substituted by organic substituted groups such as epoxy groups, acrylic groups, alkenyl groups, silanol groups, amino groups, or combinations thereof.

(A-4)

In one embodiment, the organic-inorganic metal oxide hybrid resin formed in step 106 has the following formula:

It should be noted that the formula (A-5) is merely an example. One skilled in the art would understand that the size and bonding of the oxometallate cluster structure may be various in organic-inorganic metal oxide hybrid resin according to various embodiments.

In various embodiments, the organic-inorganic metal oxide hybrid resin may have the following formula (A-6):

(A-6)

In formula (A-6), each $R^1$ is independently a substituted or non-substituted $C_1$ to $C_{10}$ alkyl group; each $R^2$ is independently a substituted or non-substituted $C_1$ to $C_{10}$ alkyl group or benzyl group; and n is a positive integer from 3 to 30. In addition, each Y is independently $(MO_{4/2})_l[(MO)_{(4-a)/2}M(OH)_{a/2}]_m[MO_{(4-b)/2}M(OZ)_{b/2}]_p$, wherein M is a metal; l is a positive integer from 10 to 90; m is a positive integer from 2 to 20; p is a positive integer from 4 to 15; a is a positive integer from 1 to 2; b is a positive integer from 1 to 2; and Z is an organosilane group. Accordingly, the structure containing repetitive siloxane units forms a main chain of the organic-inorganic metal oxide hybrid resin, and two sides of the structure containing repetitive siloxane units each bond to one oxometallate cluster structure (that is, one side of the structure containing repetitive siloxane units bonds to one oxometallate cluster structure, and the other side of the structure containing repetitive siloxane units bonds to another oxometallate cluster structure). In addition, the organosilane bonds to the outer surface (the terminal structures) of the oxometallate cluster structures.

In one embodiment, each $R^1$ is independently a $C_1$ to $C_3$ alkyl group, and each $R^2$ is independently a $C_1$ to $C_6$ alkyl group or a benzyl group. In another embodiment, M is Titanium (Ti), Zirconium (Zr), or Zinc (Zn). In still another embodiment, Z has the following formula (A-7):

(A-5)

(A-7)

In formula (A-7), $R^3$ is a $C_1$ to $C_{10}$ alkyl group containing an organic substituted group, wherein the organic substituted group comprises an expoxy group, an acrylic group, an alkenyl group, a silanol group, an amino group, or combinations thereof; ξ represents a bond, wherein the bond bonds to the Si or M of another organosilane group.

In one embodiment, the micro-crystalline structure of organic-inorganic metal oxide hybrid resin can be confirmed by Fast Fourier Transform (FFT) of Field Emission Transmission Electron Microscopy (FETEM). Therefore, the organic-inorganic metal oxide hybrid resin may be a transparent glutinous liquid having a controllable refractivity of between 1.6 and 1.95. In addition, a weight-average molecular weight of the organic-inorganic metal oxide hybrid resin may be between 8000 and 30000. In one embodiment, the organic-inorganic metal oxide hybrid resin may be used as a curing agent or a catalyst for epoxy resin.

Figure 2:
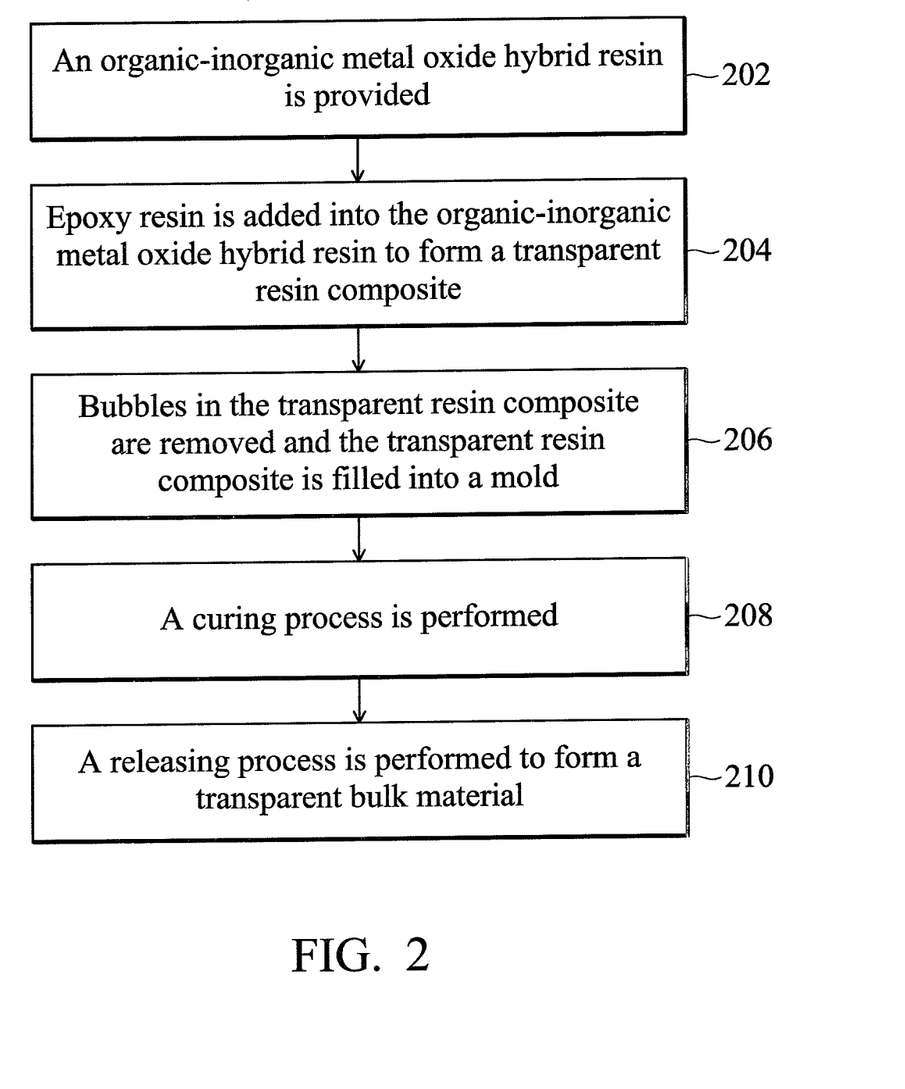
FIG. 2 illustrates a flow chart of a method for forming a transparent resin composite using the organic-inorganic metal oxide hybrid resin described above according to one embodiment.

FIG. 2 illustrates a flow chart of a method for forming a transparent resin composite using the organic-inorganic metal oxide hybrid resin described above according to one embodiment. In step 202, an organic-inorganic metal oxide hybrid resin is provided. In step 204, epoxy resin is added into the organic-inorganic metal oxide hybrid resin to form a transparent resin composite. In step 206, bubbles in the transparent resin composite are removed and the transparent resin composite is filled into a mold. In step 208, a curing process is performed. In step 210, a releasing process is performed to form a transparent bulk material.

In step 202, the organic-inorganic metal oxide hybrid resin may be the organic-inorganic metal oxide hybrid resin in various embodiments described previously. For example, the organic-inorganic metal oxide hybrid resin may be the organic-inorganic metal oxide hybrid resin formed by the method showed in FIG. 1. The organic-inorganic metal oxide hybrid resin remains to be transparent glutinous liquid after the solvent is removed. Therefore, the organic-inorganic metal oxide hybrid resin can be evenly mixed with liquid epoxy resin to form the composite in the following processes.

In step 204, epoxy resin is added into the organic-inorganic metal oxide hybrid resin to form a transparent resin composite. In one embodiment, the transparent resin composite may comprise 10 to 80 parts by weight of the organic-inorganic metal oxide hybrid resin and 20 to 90 parts by weight of liquid epoxy resin. The liquid epoxy resin comprises bisphenol A type epoxy, cycloaliphatic epoxy, cycloaliphatic modified siloxane, or combinations thereof. In one embodiment, weight-average molecular weight of the liquid epoxy resin is between 200 and 20000. In another embodiment, a viscosity of the liquid epoxy resin is between 100 cps and 30000 cps.

In addition, in step 204, 0.01 to 1 parts by weight of an additive may also be added into the mixture. Examples of the additive include, but are not limited to, a cocatalyst, a fluorescent whitening agent, an antioxidant, or combinations thereof. The cocatalyst may be, but are not limit to, a cocatalyst containing aluminum complex. Examples of the antioxidant include, but are not limited to, a hindered phenol compound, an organophosphorus compound, or combinations thereof.

Furthermore, after the transparent resin composite is formed in step 204, the solvent can be removed before de-aerating the transparent resin composite (step 206). Then, the transparent resin composite is filled into a mold. The solvent may be removed by stirring the transparent resin composite under 30° C. to 60° C. for 30 minutes to 60 minutes. Then, the de-aerating process may be performed under vacuum for 1 hr to 2 hrs.

In step 208, a curing process is performed. The curing process may be performed at 80° C. to 100° C. for 1 hr to 3 hrs and the process further performed at 110° C. to 150° C. for 1 hr to 3 hrs. After that, a releasing process is performed to form a transparent bulk material (step 210). In one embodiment, the transparent resin composite forms a transparent bulk material having a thickness of between 0.5 mm and 3 mm, and a refractive index of the transparent bulk material is between 1.45 and 1.80. In addition, the haze of the transparent bulk material can be adjusted by adjusting the amount of the organic-inorganic metal oxide hybrid resin therein. For example, a haze of the transparent bulk material may be between 10% and 80%. The transparent bulk material may retain good transmittance even when it has a larger thickness. For example, the transmittance of the total transparent bulk material may be greater than 90%.

The transparent resin in various embodiments may have a higher refractive index and transmittance than a conventional transparent resin. The conventional transparent resin formed by chemical synthesis may have organic functional groups in its molecular structure, such as aromatic rings, halogens, sulfur, or the like, resulting in worsening the transmittance and the thermal and yellowing resistance of the material. However, these organic functional groups are not used in the process of forming the transparent resin in various embodiments of the disclosure. Instead, an increase of the refractive index of the transparent resin may be achieved by adding inorganic structures onto the resin structures. These inorganic structures have the ability to increase the refractive index without causing the material to be yellowed.

In addition, when the conventional transparent resin is formed by an organic-inorganic dispersion technique, an intensive mechanical shearing force is required to disperse the nano-inorganic oxide into the transparent organic material matrix. However, the nano-inorganic oxide may still not be able to be evenly dispersed into the transparent organic material matrix. Moreover, when the material contains too much nano-inorganic oxide or when a thickness of the material is too large, the transmittance of the material will decrease notably. Therefore, its applications are limited. On the other hand, the transparent hybrid resin in various embodiments of the disclosure is in its liquid phase (even after the solvent is removed) and has modified terminal groups (modified by organosilane). Therefore, the hybrid resin and the epoxy resin could be mixed evenly without forming incompatible interfaces, and the problems of assembly of the nano-inorganic oxide in the conventional manufacturing process will not occur.

In addition, in various embodiments of the disclosure, the haze of the transparent bulk material may be adjusted by controlling the amount of transparent hybrid resin in the epoxy resin, while the transparent bulk material can still retain its high transmittance. The transparent resin composite may also be used as packaging materials or as a lens in an optical device or module to have a higher luminous efficacy and more uniform light.

Example 1

Synthesis of the Organic-Inorganic Metal Oxide Hybrid Resin QR-1

(1) 15.7 g of zirconium butoxide ($Zr(OBu)_4$; bought from Gelest) and 125 g of butanol were added into a three-necked reaction flask (1 L) and the mixture was stirred continuously. Another mixture containing 0.30 g of silanol terminated polydimethylsiloxanes, 0.005 g of ammonium hydroxide, and 45 g of butanol was prepared and was slowly added into the three-necked reaction flask. The mixture was then stirred at 40° C. for 64 hrs. The product was analyzed by Fourier transform infrared spectroscopy (FT-IR), and the result showed that the absorption peak at 950 $cm^{-1}$ disappeared. In other words, Si—O—Zr bonding had been formed.

(2) 500 g of butanol was added into the flask to dilute the mixture. Then, a mixture of 0.12 g of NH$_4$OH, 0.59 g of distilled water, and 108 g of butanol was prepared and added into the solution in step (1) to perform a reaction at 60° C. for 16 hrs.

(3) The temperature of the flask was raised to 100° C. and heated for 24 hrs. After heating, 130 g of toluene was added into the flask.

(4) The temperature of the flask was then raised to 125° C. for 72 hrs. Next, 3.6 g of the 3-glycidoxypropyltrimethoxysilane (Z-6040; bought from Dow Corning) was added into the flask. The reaction continued at 125° C. for 24 hrs. After that, the solvent was removed. A transparent glutinous liquid was obtained, and its refractivity was 1.672.

Example 2

Synthesis of the Organic-Inorganic Metal Oxide Hybrid Resin QR-2

(1) 26.2 g of zirconium butoxide (Zr(OBu)$_4$; bought from Gelest) and 125 g of butanol were added into a three-necked reaction flask (2 L) and the mixture was stirred continuously. Another mixture containing 0.30 g of silanol terminated polydimethylsiloxanes, 0.005 g of ammonium hydroxide, and 45 g of butanol was prepared and was slowly added into the three-necked reaction flask. The mixture was then stirred at 40° C. for 64 hrs. The product was analyzed by Fourier transform infrared spectroscopy (FT-IR), and the result showed that the absorption peak at 950 cm$^{-1}$ disappeared. In other words, Si—O—Zr bonding had been formed.

(2) 500 g of butanol was added into the flask to dilute the mixture. Then, a mixture of 0.192 g of NH$_4$OH, 0.98 g of distilled water, and 108 g of butanol was prepared and added into the solution in step (1) to perform a reaction at 60° C. for 16 hrs.

(3) The temperature of the flask was raised to 100° C. and heated for 24 hrs. After heating, 130 g of toluene was added into the flask.

(4) The temperature of the flask was then raised to 125° C. for 72 hrs. Next, 6.3 g of the 3-glycidoxypropyltrimethoxysilane (Z-6040; bought from Dow Corning) was added into the flask. The reaction continued at 125° C. for 24 hrs. After that, the solvent was removed. A transparent glutinous liquid was obtained, and its refractivity was 1.756.

Example 3

Synthesis of the Organic-Inorganic Metal Oxide Hybrid Resin QR-3

(1) 18.6 g of titanium butoxide (Ti(OBu)$_4$; bought from Aldrich) and 125 g of butanol were added into a three-necked reaction flask (2 L) and the mixture was stirred continuously. Another mixture containing 0.15 g of silanol terminated polydimethylsiloxanes, 0.005 g of ammonium hydroxide, and 65 g of butanol was prepared and was slowly added into the three-necked reaction flask. The mixture was then stirred at 40° C. for 64 hrs. The product was analyzed by Fourier transform infrared spectroscopy (FT-IR), and the result showed that the absorption peak at 950 cm$^{-1}$ disappeared. In other words, Si—O—Ti bonding had been formed.

(2) 500 g of butanol was added into the flask to dilute the mixture. Then, a mixture of 0.636 g of NH$_4$OH, 2.95 g of distilled water, and 120 g of butanol was prepared and added into the solution in step (1) to perform a reaction at 60° C. for 16 hrs.

(3) The temperature of the flask was raised to 100° C. and heated for 24 hrs. After heating, 130 g of toluene was added into the flask.

(4) The temperature of the flask was then raised to 125° C. for 72 hrs. Next, 4.0 g of the 3-glycidoxypropyltrimethoxysilane (Z-6040; bought from Dow Corning) was added into the flask. The reaction continued at 125° C. for 24 hrs. After that, the solvent was removed. A transparent glutinous liquid was obtained, and its refractivity was 1.903.

Example 4

Preparation for Transparent Resin Composite 1

(1) 18 g of epoxy resin SEP-A ((EpoxycyclohexylethylMethylsiloxane) Dimethylsiloxane Copolymers; EEW=570; Mw=8000~10000) and 2 g of the organic-inorganic metal oxide hybrid resin QR-1 were added into a reactor. The mixture was mixed in the reactor at room temperature for 20 minutes.

(2) The temperature of the reactor was raised to 50° C., and the solvent was removed while stirring.

(3) under vacuum environment for 1 hr.

(4) The resin material was filled into a mold and was heated in an oven at 100° C. for 2 hrs. After that, the material was heated at 130° C. for another 2 hrs to perform a curing process.

(5) A releasing process was performed to obtain the product. The resulting product contained 10 wt % of QR-1 and 90 wt % of SEP-A.

Example 5

Preparation for Transparent Resin Composite 2

(1) 16 g of SEP-A and 4 g of the organic-inorganic metal oxide hybrid resin QR-1 were added into a reactor. The mixture was mixed in the reactor at room temperature for 20 minutes.

(2) The temperature of the reactor was raised to 50° C., and the solvent was removed while stirring.

(3) A de-aerating process was performed to the resin material under vacuum environment for 1 hr.

(4) The resin material was filled into a mold and was heated in an oven at 100° C. for 2 hrs. After that, the material was heated at 130° C. for another 2 hrs to perform a curing process.

(5) A releasing process was performed to obtain the product. The resulting product contained 20 wt % of QR-1 and 80 wt % of SEP-A.

Example 6

Preparation for Transparent Resin Composite 3

(1) 14 g of SEP-A and 6 g of the organic-inorganic metal oxide hybrid resin QR-1 were added into a reactor. The mixture was mixed in the reactor at room temperature for 20 minutes.

(2) The temperature of the reactor was raised to 50° C., and the solvent was removed while stirring.

(3) A de-aerating process was performed to the resin material under vacuum environment for 1 hr.

(4) The resin material was filled into a mold and was heated in an oven at 100° C. for 2 hrs. After that, the material was heated at 130° C. for another 2 hrs to perform a curing process.

(5) A releasing process was performed to obtain the product. The resulting product contained 30 wt % of QR-1 and 70 wt % of SEP-A.

Example 7

Preparation for Transparent Resin Composite 4

(1) 10 g of SEP-A and 10 g of the organic-inorganic metal oxide hybrid resin QR-1 were added into a reactor. The mixture was mixed in the reactor at room temperature for 20 minutes.
(2) The temperature of the reactor was raised to 50° C., and the solvent was removed while stirring.
(3) A de-aerating process was performed to the resin material under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 50 wt % of QR-1 and 50 wt % of SEP-A.

Example 8

Preparation for Transparent Resin Composite 5

(1) 4 g of SEP-A and 16 g of the organic-inorganic metal oxide hybrid resin QR-1 were added into a reactor. The mixture was mixed in the reactor at room temperature for 20 minutes.
(2) The temperature of the reactor was raised to 50° C., and the solvent was removed while stirring.
(3) A de-aerating process was performed to the resin material under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 80 wt % of QR-1 and 20 wt % of SEP-A.

Example 9

Preparation for Transparent Resin Composite 6

(1) 17 g of epoxy resin SEP-B ((Epoxycyclohexylethyl Methylsiloxane) Dimethylsiloxane Copolymers, EEW=320, Mw=2800~2900) and 3 g of the organic-inorganic metal oxide hybrid resin QR-1 were added into a reactor. The mixture was mixed in the reactor at room temperature for 20 minutes.
(2) The temperature of the reactor was raised to 50° C., and the solvent was removed while stirring.
(3) A de-aerating process was performed to the resin material under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 15 wt % of QR-1 and 85 wt % of SEP-B.

Example 10

Preparation for Transparent Resin Composite 7

(1) 14 g of SEP-A and 6 g of the organic-inorganic metal oxide hybrid resin QR-2 were added into a reactor. The mixture was mixed in the reactor at room temperature for 20 minutes.
(2) The temperature of the reactor was raised to 50° C., and the solvent was removed while stirring.
(3) A de-aerating process was performed to the resin material under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 30 wt % of QR-2 and 70 wt % of SEP-A.

Example 11

Preparation for Transparent Resin Composite 8

(1) 6 g of diglycidyl ether of bisphenol-A (bought from Nanya) and 14 g of the organic-inorganic metal oxide hybrid resin QR-3 were added into a reactor. The mixture was mixed in the reactor at room temperature for 20 minutes.
(2) The temperature of the reactor was raised to 50° C., and the solvent was removed while stirring.
(3) A de-aerating process was performed to the resin material under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 70 wt % of QR-3 and 30 wt % of diglycidyl ether of bisphenol-A.

Comparative Example 1

Commercial Diffusion Plate

The commercial diffusion plate had a thickness of 2 mm and a haze of over 90%.

Comparative Example 2

(1) Aluminum acetylacetonate (bought from Sigma) was added into a reactor as a catalyst. Then, silanol terminated polydimethylsiloxane (DMS-S14; bought from Gelest) was added into the reactor. The mixture was stirred in the reactor at room temperature for 20 minutes.
(2) After the catalyst in step (1) was fully dissolved, epoxy resin SEP-A was added into the reactor. The mixture was stirred in the reactor at room temperature for 20 minutes.
(3) The bubbles in the resin material were removed under vacuum environment for 1 hr.
(4) The resin material was filled into a mold and was heated in an oven at 100° C. for 2 hrs. After that, the material was heated at 130° C. for another 2 hrs to perform a curing process.
(5) A releasing process was performed to obtain the product. The resulting product contained 63.54 wt % of SEP-A, 36.48 wt % of DMS-S14, and 0.07 wt % of the catalyst.

Comparative Example 3

(1) 9.5 g of bisphenol-A epoxy resin, 8.4 g of methylhexahydrophthalic anhydride (MHHPA; bought from New Japan Chemical Co.), and 0.09 g of U-cat 5003 (quaternary phosphonium bromide; bought from San-apro) were added into a reactor, and the mixture was stirred in the reactor at room temperature for 20 minutes. Then, 5.37 g of $ZrO_2$ sol (bought from Nissan Chemical) was also added into a reactor, and the mixture was stirred in the reactor at room temperature for 20 minutes.

(2) After the solvent was removed under vacuum environment, the bubbles in the resin material were removed for 1 hr.

(3) The resin material was filled into a mold and was heated in an oven at 100° C. for 2 hrs. After that, the material was heated at 130° C. for another 2 hrs to perform a curing process.

(4) A releasing process was performed to obtain the product. The resulting product contained 70 wt % of epoxy resin/MHHPA/5003 and 30 wt % of the $ZrO_2$ sol.

Optical Properties Tests

Various optical properties of the products in various examples and comparative examples were analyzed using a refractometer (ATAGO DR-M4) and a Haze meter (NIPPON DENSHOKU NDH 2000). The original refractivity of epoxy resin SEP-A was 1.43. The original refractivity of epoxy resin SEP-B was 1.48. The original refractivity of diglycidyl ether of bisphenol-A was 1.57. The refractive index of the transparent resin composite was 1.48.

Table 1 illustrates the refractivity (R.I.), haze, total transmittance (T.T.), and straight penetrate transmittance (P.T.) of products in various examples and comparative examples. As shown in Table 1, the refractive index of the commercial diffusion plate in comparative example 1 could not be measured, and the commercial diffusion plate has a low total transmittance. In comparative example 2, the main portion of the composite was epoxy resin SEP-A (with aluminum catalyst). Although the composite had a better total transmittance, it had a low refractive index. In comparative example 3, inorganic material was dispersed in organic resin. Although the composite had a better refractive index, its total transmittance was low.

On the other hand, all the transparent resin composite 2 to 8 in various examples had both good refractive index and transmittance. According to the refractive index of transparent resin composite 2 to 5, it can be seen that when the transparent resin composite contained more organic-inorganic metal oxide hybrid resin, the composite could have a higher refractive index. In addition, according to the refractive index of transparent resin composite 3 and 7, it can be seen that when the metallic oxide in the organic-inorganic metal oxide hybrid resin had a higher solid content, the refractive index of the composite could also be increased. In addition, the refractive index of the composite could also be adjusted by changing the metals in the organic-inorganic metal oxide hybrid resin. Moreover, it was found that the haze of the transparent resin composite could be adjusted by adjusting the amount of the organic-inorganic metal oxide hybrid resin in the transparent resin composite.

In addition, table I also illustrates the straight penetrate transmittance (P.T.) of products in various examples and comparative examples. Referring to comparative example 2, its values of the total transmittance and straight penetrate transmittance were close. In other examples, the straight penetrate transmittance decreased when the haze increased. However, the total transmittance of those examples remained over 90%. In other words, the products in various examples did not absorb light, and the reason for the decreased straight penetrate transmittance was because the light was diffused in many directions. Therefore, the resulting material in various examples had uniform light.

TABLE 1

|  | Refractive index | Haze(%) | T.T. (%) | P.T. (%) |
|---|---|---|---|---|
| Transparent resin composite 2 | 1.49 | 37 | 92 | 53 |
| Transparent resin composite 3 | 1.50 | 65 | 92 | 32 |
| Transparent resin composite 4 | 1.51 | 70 | 90 | 26 |
| Transparent resin composite 5 | 1.63 | 80 | 90 | 17 |
| Transparent resin composite 6 | 1.52 | 39 | 91 | 56 |
| Transparent resin composite 7 | 1.53 | 66 | 90 | 30 |
| Transparent resin composite 8 | 1.79 | 78 | 90 | 16 |
| Comparative example 1 | — | 98 | 63 | <1 |
| Comparative example 2 | 1.44 | 1.5 | 93 | 92 |
| Comparative example 3 | 1.58 | 7 | 84 | 78 |

While the disclosure has been described by way of example and in terms of the preferred embodiments, it is to be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic-inorganic metal oxide hybrid resin having the following formula:

wherein each $R^1$ is independently a substituted or non-substituted $C_1$ to $C_{10}$ alkyl group;

each $R^2$ is independently a substituted or non-substituted $C_1$ to $C_{10}$ alkyl group or benzyl group;

n is a positive integer from 3 to 30; and each Y is independently $(MO_{4/2})_l[(MO)_{(4-a)/2}M(OH)_{a/2}]_m$ $[MO_{(4-b)/2}M(OZ)_{b/2}]_p$, wherein M is a metal;

l is a positive integer from 10 to 90;

m is a positive integer from 2 to 20;

p is a positive integer from 4 to 15;

a is a positive integer from 1 to 2;

b is a positive integer from 1 to 2; and

Z is an organosilane group.

2. The organic-inorganic metal oxide hybrid resin as claimed in claim 1, wherein each $R^1$ is independently a $C_1$ to $C_3$ alkyl group, and each $R^2$ is independently a $C_1$ to $C_6$ alkyl group or a benzyl group.

3. The organic-inorganic metal oxide hybrid resin as claimed in claim 1, wherein M is Titanium (Ti), Zirconium (Zr), or Zinc (Zn).

4. The organic-inorganic metal oxide hybrid resin as claimed in claim 1, wherein Z has the following formula:

wherein R³ is a C₁ to C₁₀ alkyl group containing an organic substituted group, wherein the organic substituted group comprises an epoxy group, an acrylic group, an alkenyl group, a silanol group, an amino group, or combinations thereof; and } represents a bond, wherein the bond bonds to the Si or M of another organosilane group.

5. The organic-inorganic metal oxide hybrid resin as claimed in claim 1, wherein a weight-average molecular weight of the organic-inorganic metal oxide hybrid resin is between 8000 and 30000.

6. The organic-inorganic metal oxide hybrid resin as claimed in claim 1, wherein the organic-inorganic metal oxide hybrid resin is a transparent glutinous liquid having a refractive index of between 1.6 and 1.95.

7. The organic-inorganic metal oxide hybrid resin as claimed in claim 1, the chemical structure can has the following formula:

wherein R³ is a C₁ to C₁₀ alkyl group containing an organic substituted group, wherein the organic substituted group comprises an epoxy group, an acrylic group, an alkenyl group, a silanol group, an amino group, or combinations thereof.

8. A transparent resin composite, comprising:
    10 to 80 parts by weight of the organic-inorganic metal oxide hybrid resin as claimed in claim 1; and
    20 to 90 parts by weight of liquid epoxy resin.

9. The transparent resin composite as claimed in claim 8, wherein the liquid epoxy resin comprises bisphenol A type epoxy, cycloaliphatic epoxy, cycloaliphatic modified siloxane, or combinations thereof.

10. The transparent resin composite as claimed in claim 8, wherein a weight-average molecular weight of the liquid epoxy resin is between 200 and 20000.

11. The transparent resin composite as claimed in claim 8, wherein a viscosity of the liquid epoxy resin is between 100 cps and 30000 cps.

12. The transparent resin composite as claimed in claim 8, further comprising:
    0.01 to 1 parts by weight of an additive, wherein the additive comprises a cocatalyst, a fluorescent whitening agent, an antioxidant, or combinations thereof.

13. The transparent resin composite as claimed in claim 12, wherein the cocatalyst comprises a cocatalyst containing aluminum complex.

14. The transparent resin composite as claimed in claim 8, wherein the composite comprises an antioxidant and wherein the antioxidant comprises a hindered phenol compound, an organophosphorus compound, or combinations thereof.

15. The transparent resin composite as claimed in claim 8, wherein the transparent resin composite forms a transparent bulk material having a thickness of between 0.5 mm and 3 mm.

16. The transparent resin composite as claimed in claim 15, wherein a refractive index of the transparent bulk material is between 1.45 and 1.80.

17. The transparent resin composite as claimed in claim 14, wherein a haze of the transparent bulk material is between 10% and 80%.

18. The transparent resin composite as claimed in claim 15, wherein a total transmittance of the transparent bulk material is larger than 90%.

19. A method for forming an organic-inorganic metal oxide hybrid resin as claimed in claim 1, comprising:
    performing a bonding reaction between a metallic alcoholate precursor and a polysiloxane having a terminal organic functional group, resulting in forming a compound having an oxometallate cluster structure and a structure containing repetitive siloxane units;
    performing a sol-gel reaction by adding a catalyst and water to the compound having oxometallate cluster structures and a structure containing repetitive siloxane units to form a sol-gel product; and reacting the sol-gel product with organosilane to form an organic-inorganic metal oxide hybrid resin.

20. The method for forming an organic-inorganic metal oxide hybrid resin as claimed in claim 19, wherein the polysiloxane has the following formula:

wherein $R^1$ is a substituted or non-substituted $C_1$ to $C_{10}$ alkyl group;

$R^2$ is a substituted or non-substituted $C_1$ to $C_{10}$ alkyl group or benzyl group; and n is a positive integer from 3 to 30.

21. The method for forming an organic-inorganic metal oxide hybrid resin as claimed in claim 19, wherein the metallic alcoholate precursor comprises titanium alcoholate, zirconium alcoholate, zinc alcoholate, or combinations thereof.

22. The method for forming an organic-inorganic metal oxide hybrid resin as claimed in claim 21, wherein the metallic alcoholate precursor comprises n-butyl zirconium, n-butyl titanium, n-butyl zinc, or combinations thereof.

23. The method for forming an organic-inorganic metal oxide hybrid resin as claimed in claim 19, wherein the step of performing the sol-gel reaction further comprises using a solvent, wherein the solvent comprises butanol, isopropyl alcohol, toluene, hexane, or combinations thereof.

24. The method for forming an organic-inorganic metal oxide hybrid resin as claimed in claim 19, wherein the organosilane contains an expoxy group, an acrylic group, an alkenyl group, a silanol group, or an amino group.

25. The method for forming an organic-inorganic metal oxide hybrid resin as claimed in claim 19, wherein the structure containing repetitive siloxane units forms a main chain of the organic-inorganic metal oxide hybrid resin, and two sides of the structure containing repetitive siloxane units each bond to one oxometallate cluster structure, and the organosilane bonds to the oxometallate cluster structures.

* * * * *